(12) United States Patent
Forsberg

(10) Patent No.: US 7,988,706 B2
(45) Date of Patent: *Aug. 2, 2011

(54) TISSUE PUNCTURE CLOSURE DEVICE WITH AUTOMATIC TORQUE SENSING TAMPING SYSTEM

(75) Inventor: Andrew Thomas Forsberg, Minneapolis, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 42 days.

This patent is subject to a terminal disclaimer.

(21) Appl. No.: 11/824,255

(22) Filed: Jun. 29, 2007

(65) Prior Publication Data

US 2007/0255314 A1    Nov. 1, 2007

Related U.S. Application Data

(63) Continuation of application No. 11/103,196, filed on Apr. 11, 2005, now Pat. No. 7,250,057.

(51) Int. Cl.
 *A61B 17/08* (2006.01)
(52) U.S. Cl. .......................... 606/213; 74/113; 475/125
(58) Field of Classification Search .................. 606/213, 606/124, 139, 144–146, 232; 74/113; 475/125
See application file for complete search history.

(56) References Cited

U.S. PATENT DOCUMENTS

| | | | |
|---|---|---|---|
| 4,729,260 A * | 3/1988 | Dudden | ........................ 475/125 |
| 4,744,364 A | 5/1988 | Kensey | |
| 5,021,059 A | 6/1991 | Kensey et al. | |
| 5,222,974 A | 6/1993 | Kensey et al. | |
| 5,282,827 A | 2/1994 | Kensey et al. | |
| 5,290,310 A | 3/1994 | Makower et al. | |
| 5,324,306 A | 6/1994 | Makower et al. | |
| 5,411,520 A | 5/1995 | Nash et al. | |
| 5,431,666 A | 7/1995 | Sauer et al. | |
| 5,507,744 A | 4/1996 | Tay et al. | |
| 5,527,322 A | 6/1996 | Klein et al. | |
| 5,792,152 A | 8/1998 | Klein et al. | |
| 5,860,991 A | 1/1999 | Klein et al. | |
| 6,045,569 A | 4/2000 | Kensey et al. | |
| 6,090,130 A | 7/2000 | Nash et al. | |
| 6,179,963 B1 | 1/2001 | Begemann et al. | |
| 6,206,893 B1 | 3/2001 | Klein et al. | |
| 6,425,911 B1 | 7/2002 | Akerfeldt et al. | |
| 6,508,828 B1 | 1/2003 | Akerfeldt et al. | |
| 6,860,895 B1 * | 3/2005 | Akerfeldt et al. | ............. 606/215 |
| 2003/0060846 A1 * | 3/2003 | Egnelov et al. | ............... 606/213 |
| 2005/0085851 A1 | 4/2005 | Fiehler et al. | |

OTHER PUBLICATIONS

Information on related Patents and Patent Applications, see the section of the accompanying Information Disclosure Statement Letter entitled "Related Patents and Patent Applications" for further information, Jul. 19, 2007.

* cited by examiner

*Primary Examiner* — Gary Jackson
*Assistant Examiner* — Katherine M Dowe
(74) *Attorney, Agent, or Firm* — Holland & Hart

(57) ABSTRACT

Methods and apparatus for sealing a puncture or incision formed percutaneously in tissue separating two internal portions of the body of a living being with an anchor, a sealing plug and a filament connecting the anchor and sealing plug are disclosed. The methods and apparatus provide for automatic tamping of the sealing plug. In addition, torque required to tamp the sealing plug is automatically sensed and gear ratios of an automatic tamping device are automatically changed in response to sensed changes in torque. A planetary transmission may be used to automatically change gear ratios in response to the changes in torque.

20 Claims, 6 Drawing Sheets

US 7,988,706 B2

TISSUE PUNCTURE CLOSURE DEVICE WITH AUTOMATIC TORQUE SENSING TAMPING SYSTEM

RELATED APPLICATION

This is a continuation of U.S. patent application Ser. No. 11/103,196 filed 11 Apr. 2005 now U.S. Pat. No. 7,250,057.

FIELD OF THE INVENTION

This invention relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices, such as those described in U.S. Pat. Nos. 6,179,963; 6,090,130; and 6,045,569 and related patents that are hereby incorporated by reference.

Typical closure devices such as the ones described in the above-mentioned patents place a sealing plug at the tissue puncture site. Successful deployment of the sealing plug, however, requires that it be manually ejected from within a device sheath and tamped down to an outer surface of the tissue puncture using a tamping tube. The tamping procedure cannot commence until the device sheath (within which the tamping tube is located) has been removed so as to expose the tamping tube for manual grasping. Under certain conditions, removal of the sheath prior to tamping the sealing plug may cause the sealing plug itself to be retracted from the tissue puncture, hindering subsequent placement of the sealing plug, and resulting in only a partial seal and associated late bleeding from the tissue puncture. Accordingly, there is a need for improving the mechanism for deployment of the sealing plug at the site of a tissue puncture.

SUMMARY

The present invention meets the above-described needs and others. Specifically, the present invention provides methods and systems for closing internal tissue punctures. However, unlike prior systems, the present invention provides automatic tamping to a sealing plug as the closure device is retracted. In addition, the present invention allows the automatic tamping system to sense torque and change gear ratio when, for example, the sealing plug is passing through a small tip or other outlet.

In one of many possible embodiments, the present invention provides a tissue puncture closure device for partial insertion into and sealing of an internal tissue wall puncture. The device comprises a filament extending from a first end of the closure device to a second end of the closure device, an anchor for insertion through the tissue wall puncture attached to the filament at the second end of the closure device, a sealing plug slidingly attached to the filament adjacent to the anchor, and a tamping assembly comprising an automatic gear ratio changing transmission. The automatic gear ratio changing transmission is capable of automatically changing gear ratios in response to changes in torque. The tamping assembly may include a tamping tube operatively connected to the automatic gear ratio changing transmission.

The automatic gear ratio changing transmission may comprise a planetary gearset. The automatic gear ratio changing transmission may also comprise an input gear and an output gear coupled to the planetary gearset. The planetary gearset may comprise a ring gear, a sun gear, at least two planet gears, and a planet carrier. The input gear may be coaxially attached to a spool with a portion of the filament wound thereon, the input gear meshed with the ring gear, and the output gear meshed with the planet carrier and the tamping tube. The spool may rotate and drive the input gear in a first direction, and the output gear may drive the tamping tube in a second direction, when the anchor is deployed and the closure device is retracted from the tissue wall puncture. The planetary gearset may include a clutch having a predetermined torque breakdown value locking the ring gear to the planet carrier. The planetary gearset may provide a torque multiplying ratio between 1:1 to 1:2 upon reaching the predetermined torque breakdown value of the clutch.

According to some embodiments the tamping tube is driven by the automatic gear ratio changing transmission to tamp the sealing plug, where the automatic gear ratio changing transmission comprises a transducer for effecting a distal force on the sealing plug upon withdrawal of the closure device from the tissue wall puncture.

Another aspect of the invention provides a tissue puncture closure device for partial insertion into and sealing of a tissue puncture in an internal tissue wall accessible through a percutaneous incision. The device comprises an anchor for disposition on a distal side of the internal tissue wall, a sealing plug for disposition on a proximal side of the internal tissue wall, a filament connected between the anchor and the sealing plug, and a torque sensing, torque multiplying transmission for automatically tamping the sealing plug along the filament distally towards the anchor. The device may further comprise a tamping device operatively connected to the torque sensing, torque multiplying transmission. The torque sensing, torque multiplying transmission may comprise a storage spool onto which a proximal end of the filament is wound, an input gear connected to storage spool, the input gear and storage spool being coaxial, and a planetary gearset engaged with the input gear. An output gear may be engaged with the planetary gearset and the tamping device. Withdrawal of the closure device from the tissue puncture with the anchor bearing against the internal tissue wall may unwind the filament from the storage spool and actuate the input gear. The input gear may drive the planetary gearset, and the planetary gearset may directly or indirectly provide a tamping force to the tamping device.

Another embodiment of the invention provides a tissue puncture closure device for partial insertion into and sealing of a tissue puncture. The device includes an anchor for insertion through the tissue puncture, a filament extending from a handle to the anchor, a sealing plug slidingly attached to the filament adjacent to the anchor, and a tamping assembly for driving the sealing plug toward the anchor. The tamping assembly comprises a planetary transmission. The tamping assembly may further comprise a tamping tube slidingly disposed on the filament and operatively connected to the planetary transmission. The planetary transmission is preferably automatically actuated by retraction of the tissue puncture closure device from the tissue puncture to drive the tamping tube toward the sealing plug.

Another aspect of the invention provides a method of sealing a tissue puncture in an internal tissue wall accessible through a percutaneous incision. The method includes withdrawing a closure device from the tissue puncture, automatically transducing a motive force generated by withdrawal of the closure device in a first direction to a tamping force in a second direction with gears, and automatically changing a gear ratio of the gears in response to changes in torque generated by the motive force. The method may further comprise applying the tamping force in the second direction to a sealing plug. The method may include transferring the motive force to a tamping device that is slidingly disposed about a filament, the filament being connected to the sealing plug. The transferring may further comprise automatically unwinding the filament from a spool by deploying an anchor attached to the filament inside the tissue puncture, and withdrawing the closure device from the tissue puncture. According to some aspects, the gears comprise an input gear, a planetary gearset meshed with the input gear, and an output gear meshed with the planetary gearset. The transferring may thus comprise driving the input gear with the spool via the unwinding, driving the planetary gearset with the input gear, driving the output gear with the planetary gearset, and driving a tamping device with the output gear. The automatically changing the gear ratio may comprise automatically clutching a planetary gearset between two or more fixed relationships. For example, automatically releasing a clutch fixing a ring gear with respect to a planetary carrier of a planetary gearset at a predetermined torque level.

Another aspect of the invention provides a method of sealing a tissue puncture in an internal tissue wall accessible through a percutaneous incision. The method comprises providing a tissue puncture closure device having a carrier tube, a filament extending through the carrier tube to an anchor and to a sealing plug located proximal of the anchor for disposition and anchoring about the tissue puncture, the tissue puncture closure device also comprising an automatic tamping device. The method also includes inserting the tissue puncture closure device into the percutaneous incision, deploying an anchor of the closure device in the tissue puncture, at least partially withdrawing the closure device from the percutaneous incision, forcing a sealing plug of the closure device through an outlet of a carrier tube, automatically sensing torque required by the automatic tamping device to force the sealing plug distally, and automatically changing a gear ratio of the automatic tamping device in response to sensed torque. The automatically sensing torque may comprise presetting a clutch with a predetermined torque breakdown value. The automatically changing a gear ratio may also comprises providing a planetary gearset capable of changing gear ratio in response to changes in torque. The automatically sensing torque and changing a gear ratio may comprise unwinding a filament from a spool of the automatic tamping device by the withdrawing of the closure device, driving a planetary gearset with the spool, locking any two of a sun gear, a ring gear, and planet carrier with a clutch, and releasing the clutch automatically when clutch torque reaches a breakdown value. The automatically sensing torque and changing a gear ratio may also comprise unwinding a filament from a spool of the automatic transmitting device by the withdrawing of the closure device, driving a planetary gearset with the spool, driving a tamping tube linearly with the planetary gearset, locking together a ring gear and planet carrier with a first clutch, releasing the ring gear from the planet carrier with the first clutch when clutch torque reaches a breakdown value, and fixing a sun gear with a second one-way clutch. The method may comprise automatically transducing a motive force generated by the at least partially withdrawing the closure device in a first direction into a tamping force on the sealing plug in a second direction via a planetary gearset.

Another embodiment of the invention provides a tissue puncture closure device for partial insertion into and sealing of an internal tissue wall puncture comprising a filament extending from a first end of the closure device to a second end of the closure device, an anchor for insertion through the tissue wall puncture attached to the filament at the second end of the closure device, a sealing plug slidingly attached to the filament adjacent to the anchor, a tamping device adjacent to the sealing plug, and an automatic, two speed planetary transmission driven by the filament and operatively connected to the tamping device for advancing the tamping device toward the sealing plug. The automatic, two speed planetary transmission may switch between first and second speeds automatically depending on torque applied to the transmission.

Additional advantages and novel features of the invention will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

Figure 1:
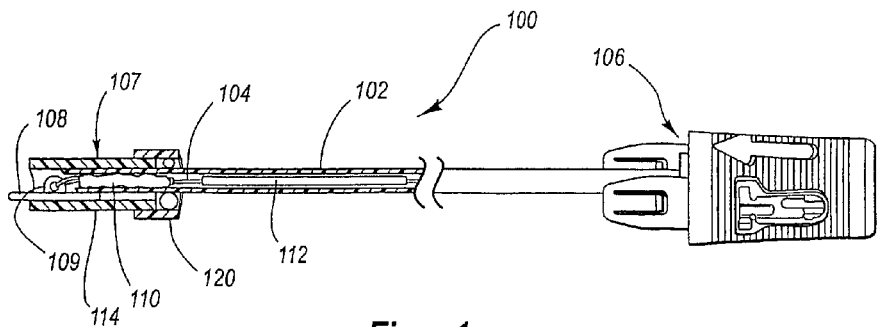
FIG. 1 is a partial cut-away view of a tissue closure device according to the prior art.

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing plug. However, sometimes the sealing plug is not properly seated against an exterior situs of the arteriotomy. If the plug does not seat against the arteriotomy, there is a potential for elongated bleeding. The present invention describes methods and apparatus to reduce or eliminate movement or misplacement of the sealing plug with a compact device. While the vascular instruments shown and described below include insertion sheaths and puncture sealing devices, the application of principles described herein are not limited to the specific devices shown. The principles described herein may be used with any vascular closure device. Therefore, while the description below is directed primarily to arterial procedures and certain embodiments of a vascular closure device, the methods and apparatus are only limited by the appended claims.

As used in this specification and the appended claims, the term "tamp" or "tamping" is used broadly to mean packing down by one or a succession of blows or taps, but not by excessive force. A "tamping tube" is used broadly to mean any elongated device or series of devices, including any intermediate components, used alone or in combination to tamp something else directly or indirectly. "Engage" and "engageable" are also used broadly to mean interlock, mesh, or contact between two devices. "Mesh" means to interlock or contact. A "spool" is a cylinder or other device on which something else is at least partially wound. A "lumen" refers to any open space or cavity in a bodily organ or device, especially in a blood vessel. "Automatic" means no action or intervention is required by a human operator. "Transduce" means to convert a force or other input energy in one form into output energy or forces of another form or direction. The words "including" and "having," as used in the specification, including the claims, have the same meaning as the word "comprising."

Referring now to the drawings, and in particular to FIGS. 1-4, a vascular puncture closure device 100 is shown according to the prior art. The vascular puncture closure device 100 includes a carrier tube 102 with a filament or suture 104 extending at least partially therethrough. The closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4). The carrier tube 102 typically includes a tamping tube 112 disposed therein. The tamping tube 112 is slidingly mounted on the suture 104 and may be used by an operator to tamp the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 2:
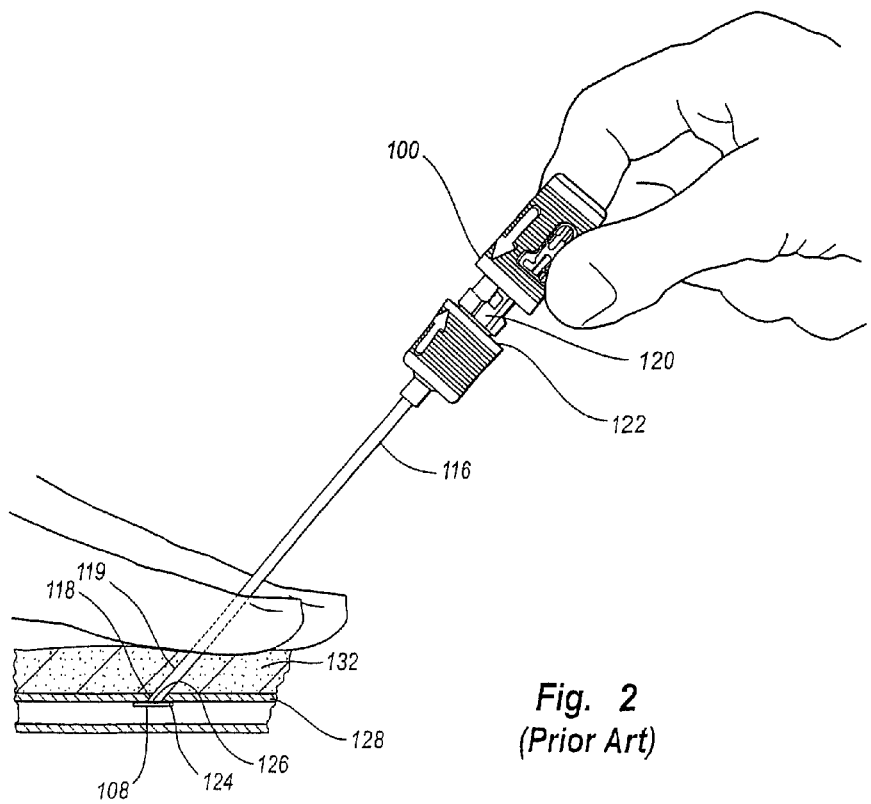
FIG. 2 is a side view of the tissue closure device of FIG. 1 engaged with an artery according to the prior art.
Figure 3:
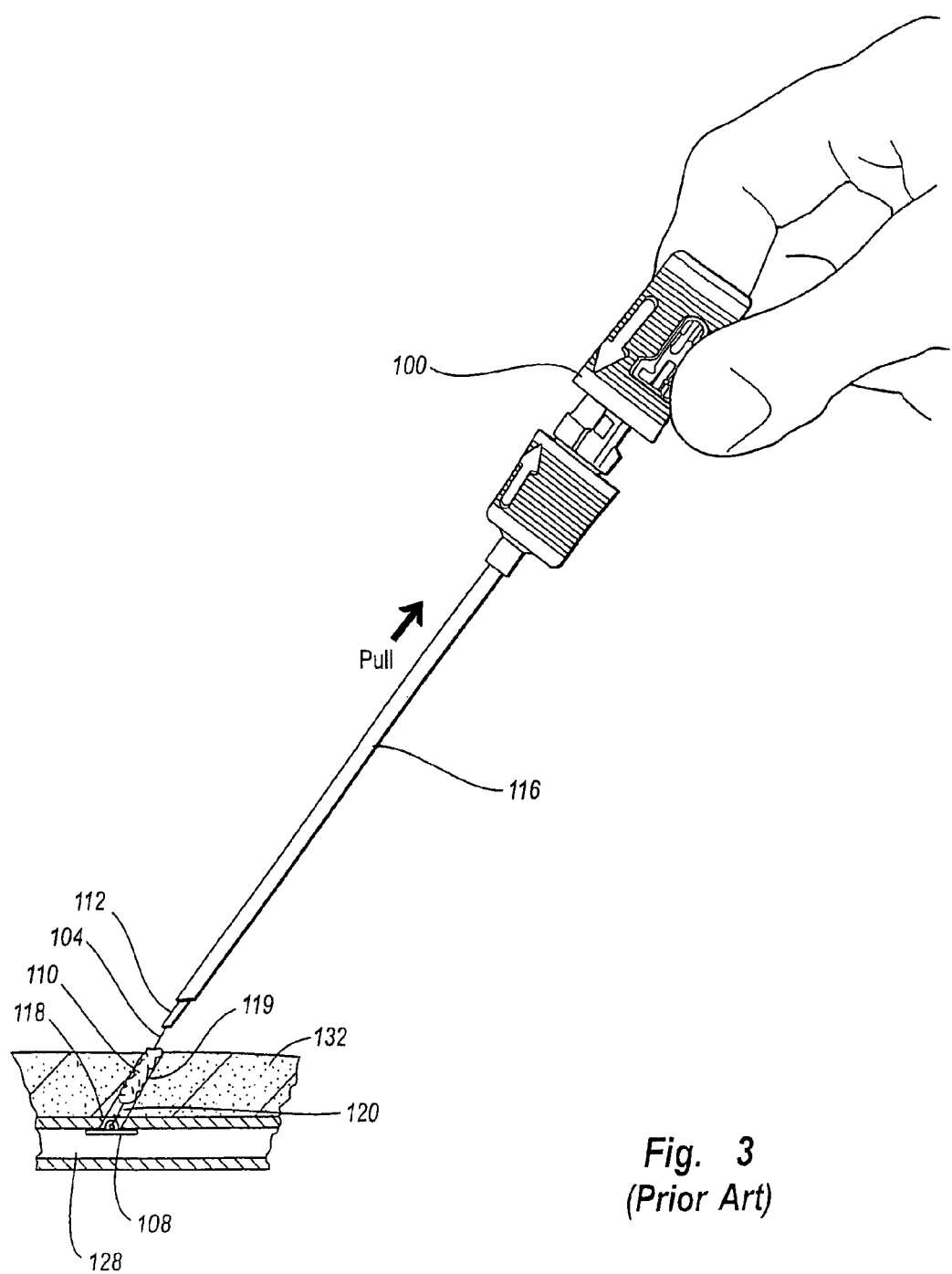
FIG. 3 is a side view of the tissue closure device of FIG. 1 being withdrawn from an artery according to the prior art to deploy a collagen sponge.
Figure 4:
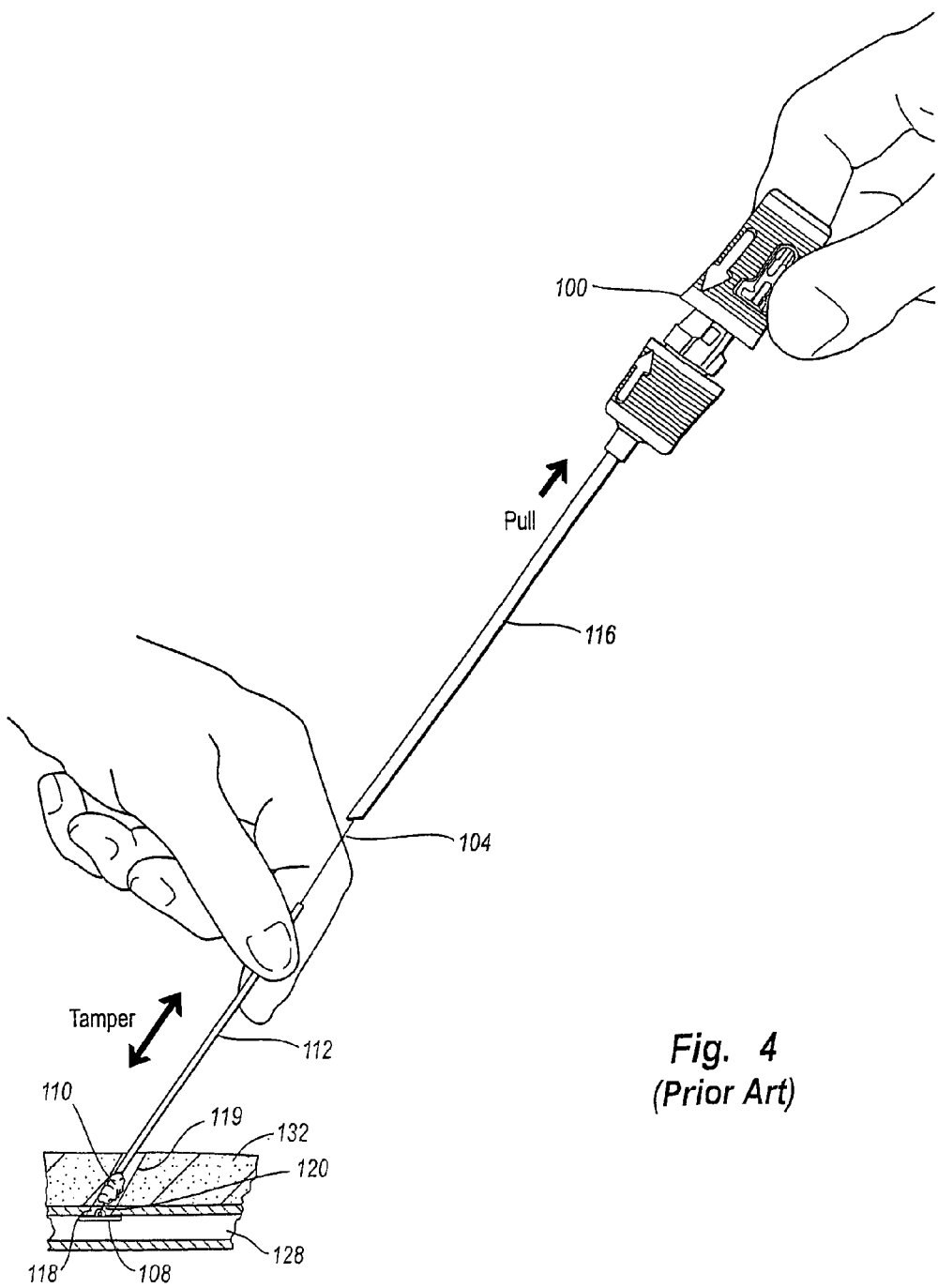
FIG. 4 is a side view of the tissue closure device of FIG. 1 illustrating tamping of the collagen sponge according to the prior art.

The flush arrangement of the anchor 108 and carrier tube 102 allows the anchor 108 to be inserted into an insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the puncture closure device 100 is inserted into the insertion sheath 116, the oversized head 120 bears against a surface 122 of insertion sheath 116. Further insertion of the puncture closure device 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 thereof. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, forcing the collagen pad 110 through the tip of the carrier tube 102 and depositing it in the incision tract 119. The tamping tube 112 is also exposed. With the tamping tube 112 fully exposed as shown in FIG. 4, the collagen pad 110 is manually tamped, and the anchor 108 and collagen pad 110 are cinched together and held in place with the self-tightening slip-knot on the suture 102. Thus, the tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

Using the typical tissue puncture closure device 100 described above, however, the tamping of the collagen pad 110 cannot commence until the sheath 116 has been removed so as to expose the tamping tube 112 for manual grasping. Under certain conditions, removal of the sheath 116 prior to tamping the collagen pad 110 causes the collagen pad 110 to retract from the tissue puncture 118, creating a gap 120 between the collagen pad 110 and the puncture 118. The gap 120 may remain even after tamping as shown in FIG. 4, and sometimes results in only a partial seal and bleeding from the tissue puncture 118.

Therefore, the present specification describes a tissue puncture closure device that automatically drives a sealing plug toward a tissue puncture upon withdrawal of the tissue puncture closure device from the tissue puncture site. The mechanism for automatically driving the sealing plug also includes a transmission that changes gear ratio automatically in response to change in torque. While the preferred embodiments of the tissue puncture closure device are shown and described below, the principles of the present specification may be incorporated into any of a number of tissue puncture closure devices. The specific embodiments described below are for illustrative purposes only, and are not limiting.

As described above, the general structure and function of tissue puncture closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Figure 5:
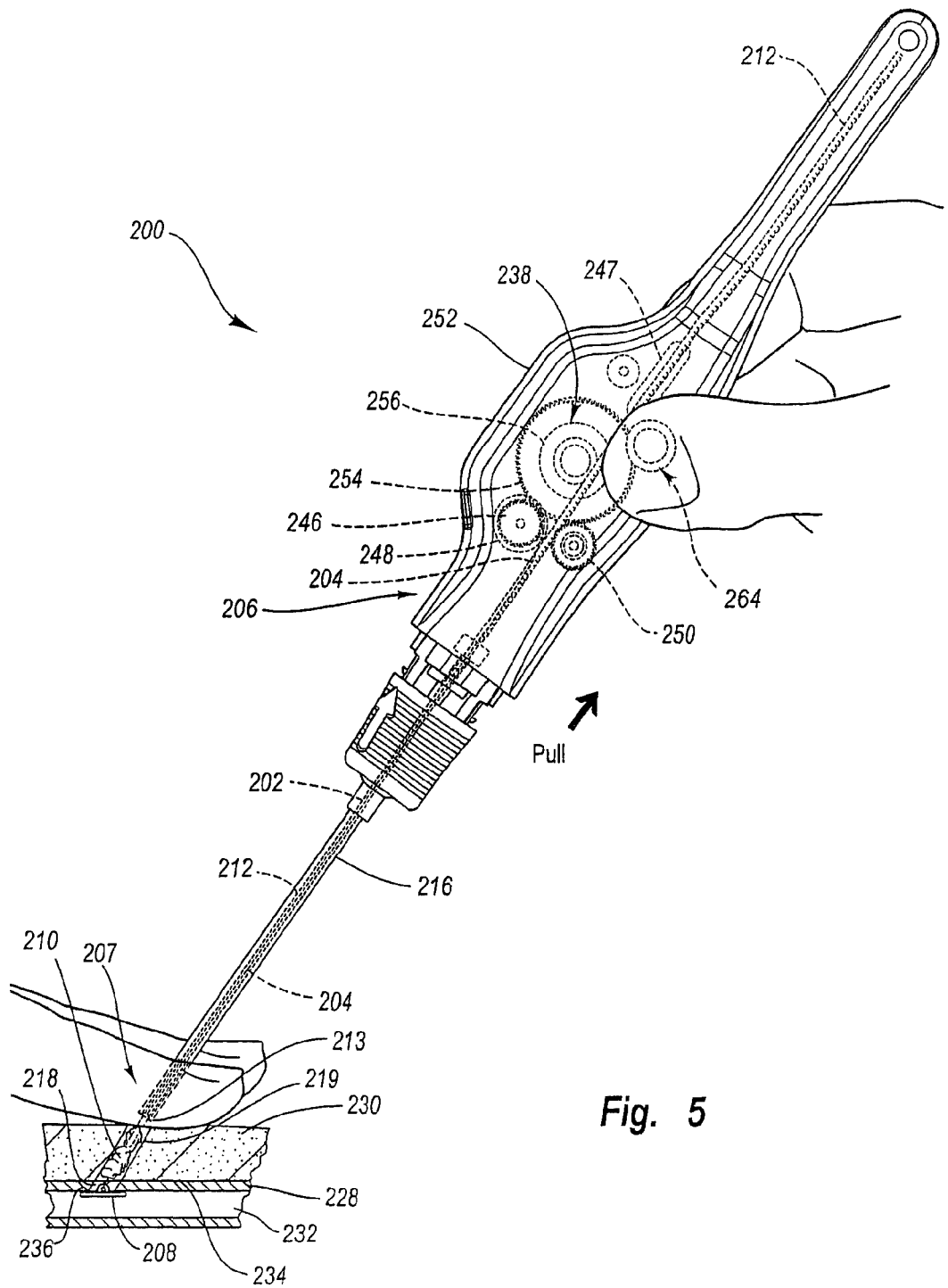
FIG. 5 is a side view of a tissue closure device with an automatic torque sensing tamping or driving mechanism shown engaged with an artery according to one embodiment of the present invention.

Referring now to FIG. 5, a tissue puncture closure device 200 is shown according to one embodiment of the present invention. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and can be used for sealing punctures or incisions in other types of tissue walls as well. Thus, the sealing of a percutaneous puncture in an artery, shown herein, is merely illustrative of one particular use of the tissue closure device 200 of the present invention.

The tissue closure device 200 includes a first or proximal end 206 and a second or distal end 207. A carrier tube 202 extends from the proximal end 206 to the distal end 207 and includes an outlet 213 at the distal end 207. The carrier tube 202 may be made of plastic or other material and is designed for insertion through a sheath 216, which is designed for insertion through a percutaneous incision 219 in a tissue layer 230 and into a lumen 232. According to FIG. 5, the lumen 232 comprises an interior portion of a femoral artery 228.

At the distal end 207 of the carrier tube 202 there is an anchor 208 and a sealing plug 210. The anchor 208 of the present embodiment is an elongated, stiff, low profile member arranged to be seated inside the artery 228 against an artery wall 234 contiguous with a puncture 218. The anchor 208 is preferably made of a biologically resorbable polymer. The sealing plug 210 is formed of a compressible sponge, foam, or fibrous mat made of a non-hemostatic biologically resorbable material such as collagen, and may be configured in any shape so as to facilitate sealing the tissue puncture 218.

The sealing plug 210 and anchor 208 are connected to one another by a filament or suture 204 that is also biologically resorbable. The anchor 208, the sealing plug 210, and the suture 204 are collectively referred to as the "closure elements" below. As shown in FIG. 5, the anchor 208 is arranged adjacent to and exterior of the distal end 207 of the sheath 216, while the sealing plug 210 is initially disposed within carrier tube 202. Although the anchor 208 is shown deployed with a first surface 236 abutting the artery wall 234, it will be understood that initially the anchor is arranged axially along the carrier tube 202 to facilitate insertion into the lumen 232 (see, for example, the anchor 108 of FIG. 1). The suture 204 extends distally from the first end 206 of the closure device 200 through the carrier tube 202. The suture 204 may be threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 may thus connect the anchor 208 and the sealing plug 210 in a pulley-like arrangement to cinch the anchor 208 and the sealing plug 210 together when the carrier tube 202 is pulled away from the anchor 208 and the sealing plug 210, sandwiching and locking the anchor 208 and plug 210 together and thereby sealing the tissue puncture 218.

The carrier tube 202 houses a tamping device, such as a tamping tube 212, for advancing the sealing plug 210 along the suture 204 and against the anchor 208. The tamping tube 212 is shown located within the carrier tube 202 and proximal of the sealing plug 208. The tamping tube 212 is preferably an elongated tubular member that may be rigid or flexible and formed of any suitable material. For example, according to one embodiment the tamping tube 212 is made of polyurethane. The suture 204 extends through or in a trough of the tamping tube 212, but is not directly connected thereto. Accordingly, the suture 204 and tamping tube 212 are free to slide past one another. According to the embodiment of FIG. 5, as the suture 204 extends beyond a proximal end of the tamping tube 212 and attaches to a tamping assembly 238, which includes the tamping tube 212, but the remainder of which is located within a housing or handle 252 at the first end 206 of the closure device 200. Embodiments of the automatic tamping assembly 238 are described in more detail below with reference to FIGS. 6 and 7.

The tamping tube 212 automatically pushes the sealing plug 210 through the outlet 213 of the carrier tube 202 upon retraction of the closure device 200 from the incision 219 when the anchor 208 is deployed as shown in FIG. 5. The tamping tube 212 or other tamping device may comprise a rack partially housed in the handle 252 and receptive of gear tines (shown in FIGS. 6 and 7). Alternatively, the tamping tube 212 may align with a separate tamping driver rack, which would then advance the tamping tube 212.

In practice, the carrier tube 202 of the closure device 200 (containing the closure elements described above) is inserted into the insertion sheath 216, which is already inserted within the artery 228. As the closure device 200 and the associated closure elements are inserted into the insertion sheath 216, the anchor 208 passes through and out of the distal end of the insertion sheath 216 and is inserted into the artery lumen 232. As mentioned above, the anchor 208 is initially arranged substantially parallel with the carrier tube 202 to facilitate insertion of the anchor 208 through the percutaneous incision 219 and into the lumen 232.

The closure device 200 is then withdrawn from the insertion sheath 216 until the anchor 208 catches on the distal end of the insertion sheath 216 and rotates to the position shown in FIG. 5. When resistance to further retraction of the closure device 200 is felt by an operator, the closure device 200 and the insertion sheath 216 are withdrawn together, causing the anchor 208 to anchor itself within the artery 228 against the artery wall 234. With the anchor 208 anchored within the artery 228 at the puncture site 218, further retraction of the closure device 200 and insertion sheath 216 forces the sealing plug 210 out through the outlet 213 in the carrier tube 202, thereby depositing the plug 210 within the incision or puncture tract 219.

However, unlike previous closure devices that require a separate, manual tamping procedure to deposit the sealing plug 210, the closure device 200 of the present invention automatically forces the sealing plug 210 out of the carrier tube 202 and tamps it toward the anchor 208. The closure device 200 drives the tamping tube 212 toward the sealing plug 210 automatically upon withdrawal of the closure device 200 from the puncture tract 219, pushing the sealing plug out of the carrier tube 202 and tamping the plug 210 toward the anchor 208. Therefore, the sealing plug 210 is tamped while the carrier tube 202 is still arranged adjacent to the puncture 218 in the femoral artery 228, reducing or eliminating any gaps that may otherwise occur between the sealing plug 210 and the puncture 218 in the femoral artery 228.

In addition, by placing tension on or pulling the suture 204 away from the puncture tract 219, the suture 204 may cinch and lock (with a slip knot or the like) together the anchor 208 and the sealing plug 210, sandwiching the artery wall 234 between the anchor 208 and sealing plug 210. The force exerted by the tamping tube 212 and the cinching together of the anchor 208 and sealing plug 210 by the filament 204 also causes the sealing plug 210 to deform radially outward within the puncture tract 219 and function as an anchor on the proximal side of the tissue puncture site 218.

However, as the sealing plug 210 is pushed through the outlet 213 of the carrier tube 202, a variable force and various amounts of torque from the automatic tamping assembly 238 may be required. Therefore, the automatic tamping assembly 238 includes an automatic transmission that changes gear ratio in response to sensed changes in torque required to advance the sealing plug 210 out of the carrier tube 202 and toward the anchor 208.

Figure 6:
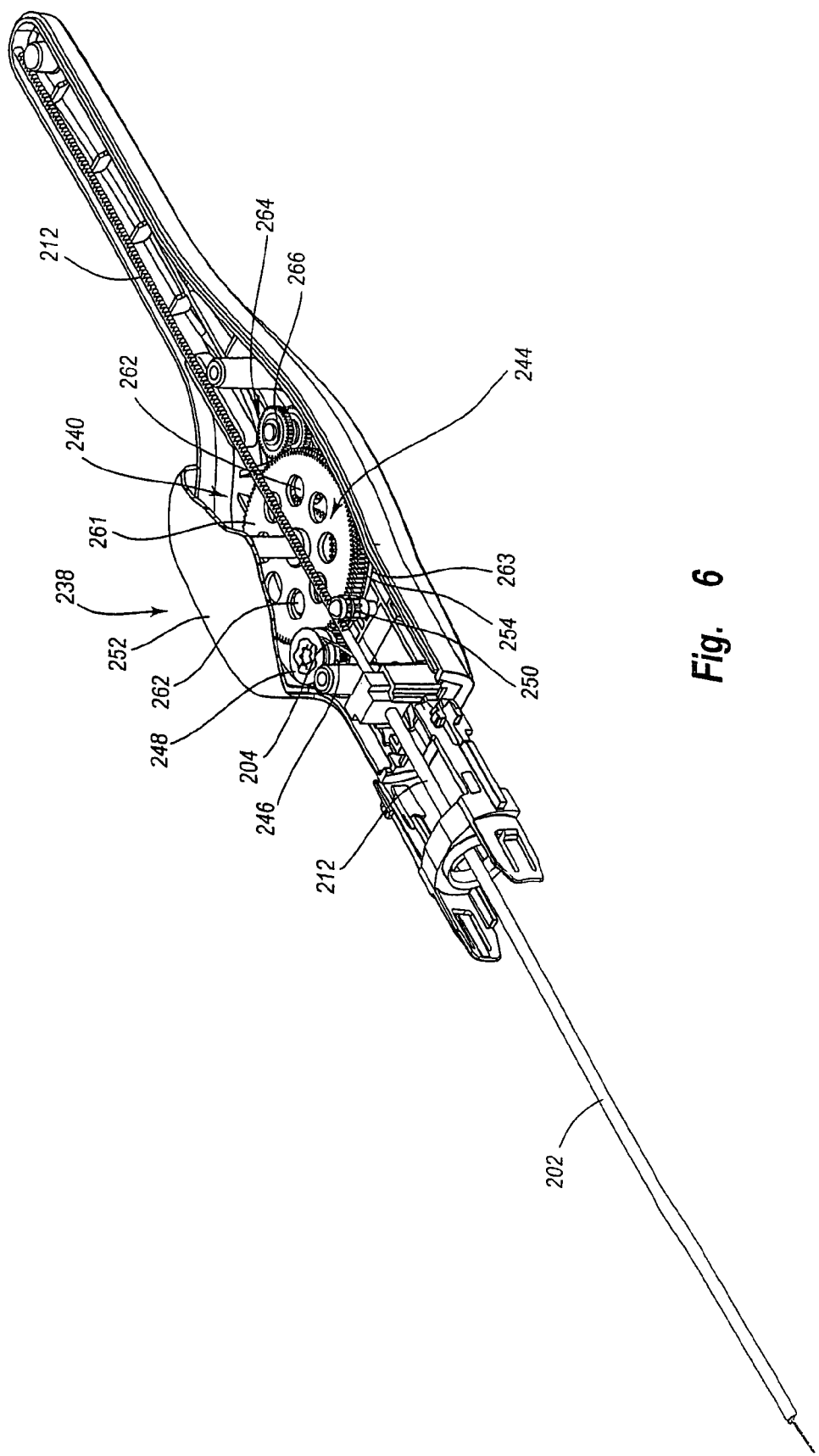
FIG. 6 is a partial assembly view of one embodiment of the torque sensing driving mechanism of FIG. 5 according to the present invention.

Automatically driving the tamping tube 212 toward the sealing plug 210 and/or cinching the plug and the anchor 208 may be facilitated by any of a number of mechanisms. For example, one automatic gear ratio changing transmission 240 that may be disposed in the housing 252 of the closure device 200 is shown in FIG. 6. The automatic gear ratio changing transmission 240 is part of the automatic tamping assembly 238. The automatic gear ratio changing transmission 240 may be a torque sensing, torque multiplying transmission as described below with reference to FIGS. 6 and 7. The automatic gear ration changing transmission 240 may comprise at least two speeds.

According to the embodiment of FIG. 6, retraction of the closure device 200 automatically effects tamping of the sealing plug 208 (FIG. 5). The retraction or motive force in a first direction is automatically transduced, according to FIG. 6, by the automatic tamping assembly 238 to a tamping force in a second direction. The details of transducing the retraction force to a tamping force are described below.

According to the automatic tamping assembly 238 of FIG. 6, the gear ratio changing transmission 240 includes a planetary gearset 244. The planetary gearset 244 is driven by an input gear 246 coupled to or engaged with the planetary gearset 244. The suture 204 is connected to and/or partially wound about a spool 248 that is coaxially attached to the input gear 246. Because the spool 248 is attached coaxially to the input gear 246, they rotate together at the same angular velocity. However, there may be a torque limiting clutch between the input gear 246 and the spool 248, such as mating fan surfaces.

Withdrawal of the closure device 200 (FIG. 5) from the tissue puncture site (if the anchor 208 (FIG. 5) is deployed) causes the suture 204 to unwind from the spool 248. The spool 248 rotates as the suture 204 unwinds and provides a torsional motive force that may be transduced to a linear tamping force.

Figure 7:
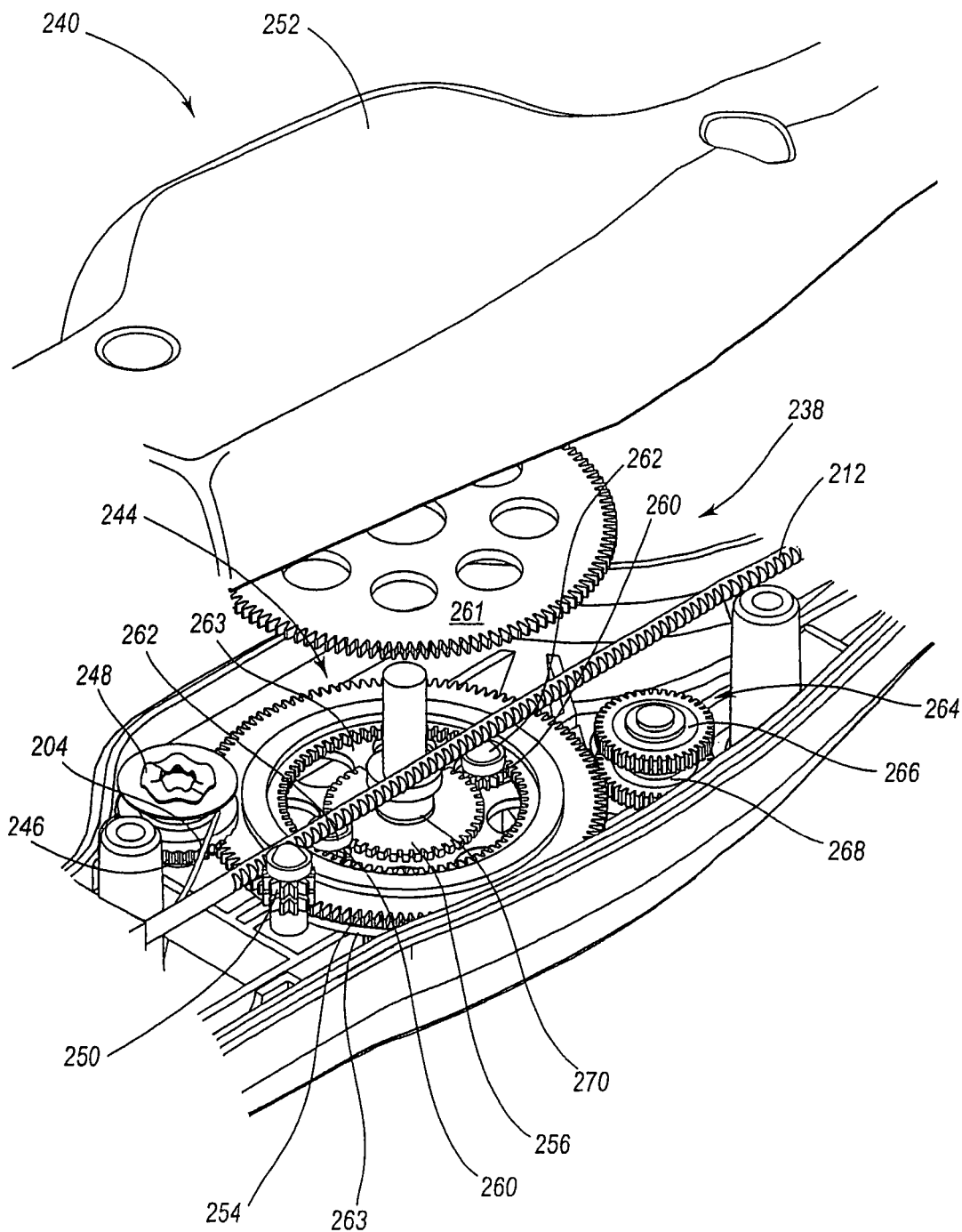
FIG. 7 is another partial assembly view of one embodiment of the torque sensing driving mechanism of FIG. 6, with a portion of a planet carrier removed for clarity.

According to the embodiment of FIGS. 6-7, the torsional motive force provided by the unwinding spool 248 is transduced into the linear tamping by the planetary gearset 244 and an output gear 250 engaged with the planetary gearset 244. The planetary gearset 244 includes a ring gear 254, a sun gear 256, a planet carrier (not separately shown), and at least two planet gears 260. The planet carrier, according to FIGS. 6-7, comprises first and second gear plates 261, 263 sandwiching the ring gear 254. The top plate 261 of the planet carrier is removed in FIG. 7 to facilitate identification of the sun gear 256 and the planet gears 260. Fasteners such as screws 262 may extend through the planet gears 260 and attach the plates 261, 263 comprising the planet carrier.

According to the embodiment of FIGS. 6-7, the input gear 246 is meshed with the ring gear 254, and the output gear 250 is meshed with the planet carrier. However, any other input/output arrangement using a planetary gearset may also be used. In addition, a first clutch 264 may fix two or more of the ring gear 254, sun gear 256, and planet carrier with respect to one another. For example, as shown in FIGS. 6-7, the first clutch 264 locks the ring gear 254 to the planet carrier. The first clutch 264 may comprise first and second preset spring-loaded plates 266, 268 that partially overlap and sandwich outer circumferential portions of the ring gear 254 and the planet carrier. The first clutch 264 thus holds the ring gear 254 and the planet carrier together in low torque situations, causing the ring gear 254 and the planet carrier to rotate together at the same angular velocity. The sun gear 256 rotates freely when the ring gear 254 is fixed to the planet carrier according to the embodiment of FIGS. 6-7. Thus, in low torque situations, the planetary gearset 244 acts as a single gear.

However, the first clutch 264 has a predetermined torque breakdown value. Accordingly, when torque applied to the ring gear 254 exceeds the predetermined torque breakdown value, the spring force of the first clutch 264 is overcome and the ring gear 254 slips with respect to the planet carrier. Thus, the first clutch 264 provides an automatic mechanical torque sensor. In addition, the sun gear 256 may include a second clutch, preferably a one-way axle mount clutch 270. Therefore, when the first clutch 264 releases ("release" includes a partial release wherein the ring gear 254 and the planet carrier slip but do not rotate freely with respect to one another, as well as free rotation), the sun gear 256 locks, and the planetary gearset 244 automatically changes gear ratio from a first speed to at least a second speed, multiplies torque applied by the input gear 246, and transmits the torque to the output gear 250. The greater the torque, the more the ring gear 254 slips and rotates relative to the planet carrier. Thus, when increased torque is required, for example, to force the sealing plug through the outlet 213 (FIG. 5) of the carrier tube 202 (FIG. 5), the first clutch 264 automatically releases and the gear ratio changes to provide additional torque. As torque decreases, the first clutch 264 reengages and returns the gear ratio to the first speed. According to some embodiments, the planetary gearset 240 provides a torque ratio between 1:1 and 1:4, preferably between about 1:1 and 1:2, upon reaching the predetermined torque breakdown value of the clutch.

According to the embodiment of FIGS. 6-7, the output gear 250 is engaged or meshed with the tamping tube 212, and the tamping tube 212 is driven linearly to distally advance and tamp the sealing plug 210 (FIG. 5). Therefore, the gears and the tamping tube 212 include mating gear teeth.

Although the embodiment of FIGS. 6-7 include an input gear 246 and an output gear 250 meshed with the planetary gearset 244, alternative embodiments may not include one or both of the input gear 246 and output gear 250. Accordingly, a spool may be directly connected to the planetary gearset 244, and one of the components of the planetary gearset 244 may be an output. Therefore, the planetary gearset 244 is operatively connected, directly or indirectly, to the tamping tube 212 or other tamping device whether or not input/output gears 246, 250 are included.

It will be understood by those of skill in the art having the benefit of this disclosure that the automatic tamping assembly 238 of FIGS. 6-7 with the planetary gearset 244 is exemplary in nature, and not limiting. Any tamping assembly that automatically changes gear ratio in response to torque requirements may be used to transmit a motive force generated by retraction of the suture 204 from the closure device 200 (FIG. 5) into a driving force for the sealing plug 210 (FIG. 5).

Operation of the embodiment of FIGS. 5-7 is as follows. As the closing device 200 is retracted from the puncture tract 219, the suture 204, which is threaded through the anchor 208, unwinds from and causes rotation of the spool 248. The spool 248 drives the input gear 246 as it rotates via the coaxial connection therebetween. As the input gear 246 rotates, it drives the planetary gearset 244, specifically the ring gear 254. The ring gear 254 is initially fixed to the planet carrier (gear plates 261/263) by the first clutch 264, and the sun gear 256 rotates freely. As long as torque produced by unwinding the suture 204 from the spool 248 remains under a predetermined value, the ring gear 254 and the planet carrier remain fixed with respect to one another. The planet carrier meshes with the output gear 250, and the output gear meshes with the tamping tube 212. The tamping tube 212 is driven distally to force the sealing plug 210 (FIG. 5) out of the carrier tube 202 (FIG. 5) and to tamp the sealing plug 210 (FIG. 5) toward the anchor 208 (FIG. 5).

However, if torque reaches a clutch breakdown value, the first clutch 264 at least partially releases the ring gear 254 from the planet carrier automatically. A second one-way clutch 270 may also lock the sun gear 256. Consequently, the ring gear 254 rotates relative to the planet carrier, causing a change in gear ratio between the input gear 246 and the output gear 250 and an additional mechanical advantage for tamping the sealing plug 210 (FIG. 5). If torque falls back below the clutch breakdown value, the first clutch 264 automatically fixes the ring gear 254 relative to the planet carrier once again. Therefore, as the closing device 200 is retracted from the puncture tract 219, the sealing plug 210 (FIG. 5) is automatically forced out of the carrier tube 202 and tamped via the automatic transmission 240 and tamping tube 212. The seal plug 210 (FIG. 5) is more likely to create a sufficient arterial seal without gaps between the sealing plug 210 (FIG. 5) and the anchor 208 (FIG. 5), as may otherwise occur with a separate manual tamping procedure. The suture 204 is ultimately cut, and the closure elements are left at the puncture site while the remainder of the closure device 200 (FIG. 5) is removed.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A tissue puncture closure device for partial insertion into and sealing of an internal tissue wall puncture, comprising:
    a filament extending from a first end of the closure device to a second end of the closure device;
    an anchor for insertion through the tissue wall puncture attached to the filament at the second end of the closure device;
    a sealing plug slidingly attached to the filament adjacent to the anchor;
    a tamping assembly to compact the sealing plug toward the anchor, the tamping assembly comprising a tamping tube and an automatic transmission, the automatic transmission comprising a filament spool about which a portion of the filament is wound, an input gear arranged coaxially with the filament spool, an output gear arranged in contact with the tamping tube, at least two intermediate gears operable between the input and output gears, and a clutch member operable to releasably engage two of the intermediate gears with each other, the automatic transmission being operable to automatically change a gear ratio between the input and output gears for achieving an additional mechanical advantage when a torque of the automatic transmission exceeds a clutch breakdown value to increase a force applied to the sealing plug by the tamping tube, and automatically decrease a mechanical advantage when the torque falls below the clutch breakdown value.

2. A tissue puncture closure device for partial insertion into and sealing of an internal tissue wall puncture according to claim 1 wherein an axis of rotation of the input, output and at least two intermediate gears are arranged parallel with an axis of rotation of the filament spool.

3. A tissue puncture closure device for partial insertion into and sealing of an internal tissue wall puncture according to claim 1, wherein the at least two intermediate gears comprises a planetary gearset.

4. A tissue puncture closure device for partial insertion into and sealing of an internal tissue wall puncture according to claim 1, wherein the at least two intermediate gears comprise:
    a planetary gearset coupled to the input gear;
    the output gear being coupled to the planetary gearset.

5. A tissue puncture closure device for partial insertion into and sealing of an internal tissue wall puncture according to claim 1, wherein the at least two intermediate gears comprise:
    a planetary gearset comprising a ring gear, a sun gear, at least two planet gears, and a planet carrier;
    the input gear meshes with the ring gear;
    the output gear meshes with the planet carrier and the tamping tube.

6. A tissue puncture closure device for partial insertion into and sealing of an internal tissue wall puncture, comprising:
    a filament extending from a first end of the closure device to a second end of the closure device;
    an anchor for insertion through the tissue wall puncture attached to the filament at the second end of the closure device;
    a sealing plug slidingly attached to the filament adjacent to the anchor;
    a tamping assembly to compact the sealing plug toward the anchor, the tamping assembly comprising a tamping tube and an automatic transmission, the automatic transmission comprising a filament spool about which a portion of the filament is wound, a plurality of gears, with an input gear arranged coaxial with the filament spool and out of contact with the tamping tube, an output gear arranged in contact with the tamping tube, and a plurality of intermediate gears, and a clutch having a predetermined torque breakdown value releasably engaging at least two of the plurality of gears with each other, the automatic transmission being operable to automatically change a gear ratio between the input and output gears for achieving an additional mechanical advantage when a torque of the automatic transmission exceeds the clutch breakdown value to increase a force applied to the sealing plug, and automatically decrease a mechanical advantage when the torque falls below the clutch breakdown value.

7. A tissue puncture closure device for partial insertion into and sealing of an internal tissue wall puncture according to claim 6 wherein an axis of rotation of the plurality of gears are arranged parallel with an axis of rotation of the filament spool.

8. A tissue puncture closure device for partial insertion into and sealing of an internal tissue wall puncture according to claim 6, wherein the plurality of intermediate gears comprises a planetary gearset, wherein gears of the planetary gearset rotate about axes that are arranged parallel with an axis of rotation of the filament spool.

9. A tissue puncture closure device for partial insertion into and sealing of an internal tissue wall puncture according to claim 6, wherein the plurality of intermediate gears comprises:
- a planetary gearset coupled to the input gear;
- the output gear coupled to the planetary gearset.

10. A tissue puncture closure device for partial insertion into and sealing of an internal tissue wall puncture according to claim 6, wherein the plurality of intermediate gears comprises:
- a planetary gearset comprising a ring gear, a sun gear, at least two planet gears, and a planet carrier;
- the input gear coaxially attached to a spool with a portion of the filament wound thereon, the input gear meshed with the ring gear;
- the output gear meshed with the planet carrier and the tamping tube.

11. A tissue puncture closure device for partial insertion into and sealing of an internal tissue wall puncture, comprising:
- a filament extending from a first end of the closure device to a second end of the closure device;
- an anchor for insertion through the tissue wall puncture attached to the filament at the second end of the closure device;
- a sealing plug slidingly attached to the filament adjacent to the anchor;
- a tamping assembly to compact the sealing plug toward the anchor, the tamping assembly comprising a tamping tube and an automatic transmission, the automatic transmission comprising a filament spool about which a portion of the filament is wound, a plurality of gears including an input gear, an output gear, and a plurality of intermediate gears, and at least one clutch operable between at least two of the plurality of gears, the automatic transmission being configured to automatically change a gear ratio between the input and output gears for achieving an additional mechanical advantage when a torque of the automatic transmission exceeds a clutch breakdown value and for achieving a decreased mechanical advantage when the torque falls below the clutch breakdown value.

12. A tissue puncture closure device for partial insertion into and sealing of an internal tissue wall puncture according to claim 11, wherein the plurality of intermediate gears comprises:
- a planetary gearset coupled to the input gear;
- the output gear coupled to the planetary gearset.

13. A tissue puncture closure device for partial insertion into and sealing of an internal tissue wall puncture according to claim 11, wherein the plurality of intermediate gears comprises:
- a planetary gearset comprising a ring gear, a sun gear, at least two planet gears, and a planet carrier;
- the input gear coaxially attached to the filament spool with a portion of the filament wound thereon, the input gear meshed with the ring gear;
- the output gear meshed with the planet carrier and the tamping tube.

14. A tissue puncture closure device for partial insertion into and sealing of an internal tissue wall puncture, comprising:
- a filament;
- an anchor for insertion through the tissue wall puncture attached to one end of the filament;
- a sealing plug slidingly attached to the filament;
- a tamping assembly to compact the sealing plug toward the anchor, the tamping assembly comprising a tamping tube and an automatic transmission, the automatic transmission comprising a filament spool, an input gear, an output gear, and at least one intermediate gear, the automatic transmission being configured to automatically change a gear ratio between the input and output gears for achieving an additional mechanical advantage when a torque of the automatic transmission exceeds a clutch breakdown value and for achieving a decreased mechanical advantage when the torque falls below the clutch breakdown value.

15. A tissue puncture closure device for partial insertion into and sealing of an internal tissue wall puncture according to claim 14, wherein the automatic transmission includes at least one clutch feature operable between the at least one intermediate gear and at least one of the input and output gears.

16. A tissue puncture closure device for partial insertion into and sealing of an internal tissue wall puncture according to claim 14, wherein the at least one intermediate gear assembly includes a planetary gear set.

17. A tissue puncture closure device for partial insertion into and sealing of an internal tissue wall puncture according to claim 16, wherein the planetary gear set includes a ring gear, a sun gear, at least two planet gears, and a planet carrier, the input gear being meshed with the ring gear, and the output gear being meshed with the planet carrier.

18. A tissue puncture closure device, comprising:
- an anchor;
- a sealing plug;
- a filament coupled to the anchor and sealing plug;
- an automatic transmission comprising at least a filament spool having a portion of the filament wound thereon, an input gear, an output gear, and at least one intermediate gear, the automatic transmission being configured to automatically change a gear ratio between the input and output gears for achieving an additional mechanical advantage when a torque of the automatic transmission exceeds a clutch breakdown value and for achieving a decreased mechanical advantage when the torque falls below the clutch breakdown value;
- wherein the tissue puncture closure device is operable to compact the sealing plug towards the anchor to seal tissue puncture closed.

19. A tissue puncture closure device according to claim 18, wherein the automatic transmission includes a tamping tube, and the automatic transmission being operable to advance the tamping tube to compact the sealing plug.

20. A tissue puncture closure device according to claim 18, wherein the at least one intermediate gear includes a planetary gear set comprising a ring gear, a sun gear, at least two planet gears, and a planet carrier, wherein the input gear is meshed with the ring gear and the output gear is meshed with the planet carrier.

* * * * *